US005972880A

United States Patent [19]
Pelletier et al.

[11] Patent Number: 5,972,880
[45] Date of Patent: Oct. 26, 1999

[54] METHOD OF TREATMENT OF OSTEOARTHRITIS WITH INTERLEUKEN-1 RECEPTOR ANTAGONIST

[75] Inventors: Jean-Pierre Pelletier; Johanne Martel-Pelletier, both of St-Lambert, Canada

[73] Assignee: Arthro Lab Inc., Sherbrooke, Canada

[21] Appl. No.: 08/612,433

[22] Filed: Mar. 7, 1996

[51] Int. Cl.$^6$ .......................... A61K 38/17; C07K 14/47
[52] U.S. Cl. .................................. 514/2; 514/8; 514/12; 514/885; 424/84; 424/184.1; 424/198.1; 530/350
[58] Field of Search ............................ 514/2, 8, 12, 885; 424/84, 85.1, 184.1, 198.1, 85.2; 530/350

[56] References Cited

U.S. PATENT DOCUMENTS

| | | | |
|---|---|---|---|
| 5,075,222 | 12/1991 | Hannum et al. | 435/69.1 |
| 5,508,262 | 4/1996 | Norman, Jr. | 514/8 |

OTHER PUBLICATIONS van Beuningen HM, et al.: Transforming growth factor–beta 1 stimulates articular chondrocyte proteoglycan synthesis and induces osteophyte formation in the murine knee joint. Lab Invest 71:279–290, 1994.

Arend WP: Growth factors and cytokines in the rheumatic diseases. In, Primer on the Rheumatic Diseases. Tenth edition. Edited by HR Schumacher, JH Klippel, WJ Koopman. The Arthritis Foundation, Georgia, 1993.

Vivien D. Galera P, et al.: Differential effects of transforming growth factor–beta and epidermal growth factor on the cell cycle of cultured rabbit articular chondrocytes. J Cell Physiol 143:534–545, 1990.

Frazer A. Bunning RA, et al.: Effects of transforming growth factor beta and interleukin–1 beta on [3H] thymidine incorporation by human articular chondro–cytes in vitro, Biochim Biophys Acta 1226:193–200, 1994.

Guerne PA. et al.: Growth factor responsiveness of human articular chondrocytes: distinct profiles in primary chondrocytes, subcultured chondrocytes, and fibroblasts. J Cell Physiol 158:476–484, 1994.

Pujol JP, et al. Transforming growth factor–beta (TGF–beta) and articular chondrocytes. Ann Endocrinol (Paris) 55:109–120, 1994.

Arner E. et al: Interleukin–1 receptor antagonist inhibits proteoglycan breakdown in antigen induced but not polycation induced arthritis in the rabbit. J. Rheum 22:1338–1346, 1995.

Arend WP, et al.: Inhibition of the production and effects of interleukin–1 and tumor necrosis factor α in rheumatoid arthritis. Arthritis Rheum 38:151–160, 1995.

Jean–Pierre Pelletier, et al.: In vitro effects of tiaprofenic acid, sodium salicylate and hydrocortisone on the proteoglycan metabolism of human osteo–arthritic cartilage. The Journal of Rheumatology, 1989;16:5, 646–655.

Edward C. Huskisson, et al. Effects of antiinflammatory drugs on the progression of osteoarthritis of the knee. The Journal of Rheumatology 1995: 22:10;1941–1946.

Interleukin 1 Receptor Antogonist—William P. Arend p. 1445–1451—vol. 88, Nov. 1991—J. Clin. Invest.

Arthritis & Rheumatism, vol. 38, No. 9, Suppl., 1995, New York, N.Y., US, p. S160 XP000674702, J.P. Caron et al,: Protective effects of intraarticular injections of human recombinant interleukin–1 receptor antagonist in experimental canine osteoarthritis, see abstract No. 47.

The Journal of Clinical Investigation, vol. 96, No. 5, Nov. 1995, New York, N.Y., US, pp. 2454–2460, XP000674753, V.M. Baragi et al.: Transplantation of transduced chondrocytes protects articular cartilage from interleukin 1–induced extracellular matrix degradation.

Arthritis & Rheumatism, vo. 39, No. 9, Sep. 1996, New York, N.Y. US, pp. 1535–1544, XP000674703, J.P. Caron et al,: Chondroprotective effect of intraarticular injections of interleukin–1 receptor antagonist in experimental osteoarthritis.

Pelletier JP, Howell DS: Etiopathogenesis of osteoarthritis. In, Arthritis and Allied Conditions. A Textbook of Rheumatology. Twelfth edition. Edited by DJ McCarthy, WJ Koopman. Philadelphia, Lea & Febiger, 1993, pp. 1723–1734.

Dean DD: Proteinase–mediated cartilage degradation in osteoarthritis. Semin Arthritis Rheum 20:2–11, 1991.

Pelletier JP, DiBattista JA, Roughley P. McCollum R, Martel–Pelletier J: Cytokines and inflammation in cartilage degradation. In, Osteoarthritis, Edition of Rheumatic Disease Clinics of North America. Edited by RW Moskowitz. Philadelphia, WB Saunders, 1993, vol. 19, No. 3, pp. 545–567.

Pelletier JP, McCollum R, Cloutier JM, Martel–Pelletier J: Synthesis of metalloproteases and IL–6 in human osteoarthritic synovial membrane in an IL–1 mediated process. J Rheumatol 22:109–114, 1995.

Larrick JW, Kunkel SL: The role of tumor necrosis factor and interleukin 1 in the immuno–inflammatory response. Pharm Res 5:129–139, 1988.

Goldring MB, Birkhead J. Sandell LJ, Kimura T, Krane SM: Interleukin 1 suppresses expression of cartilage–specific types II and IX collagens and increases types I and III collagens in human chondrocytes. J Clin Invest 82:2026–2037, 1988.

Tyler JA: Articular cartilage cultured with catabolin (pig interleukin 1) synthesizes a decreased number of normal proteoglycan molecules. Biochem J 227:869–878, 1985.

Dingle JT, Horner A. Shield M: The sensitivity of synthesis of human cartilage matrix to inhibition by IL–1 suggests a mechanism for the development of osteoarthritis. Cell Biochem Funct 9:99–102, 1991.

(List continued on next page.)

*Primary Examiner*—Prema Mertz
*Attorney, Agent, or Firm*—ROBIC

[57] ABSTRACT

A method and a composition for the preventative treatment of osteoarthritis comprising the periodic administration to a mammal suffering of this disease of a composition comprising an amount of Human recombinant Interleukin-1 receptor antagonist effective for reducing the progression of lesions and cartilage degradation.

3 Claims, 2 Drawing Sheets

OTHER PUBLICATIONS

Arend WP, Joslin FG, Massoni RJ: Effects of immune complexes on production by human monocytes of interleukin 1 or an interleukin 1 inhitibor. J. Immunol 134:3868–3875, 1985.

Balavoine JF, de Rochemonteix B, Williamson K, Seckinger P. Cruchaud A, Dayer JM: Prostaglandin E2 and collagenase production by fibroblasts and synovial cells is regulated by urine–derived human interleukin 1 and inhibitor(s). J. Clin Invest 78:1120–1124, 1986.

Carter DB, Deibel MR Jr, Dunn CJ, Tomich CS, Laborde AL. Slightom JL. Berger AE, Bienkowski MJ, Sun FF, McEwan RN, Harris PKW, Yem AW, Waszak GA, Chosay JG, Sieu LC, Hardee MM, Zurcher–Neely HA, Reardon IM, Heinrikson RL, Truesedell SE, Shelly JA, Eessalu TE, Taylor BM, Tracey DE: Purification, cloning, expression and biological chracterization of an interleukin–1 receptor antagonist protein. Nature 344:633–638, 1990.

Hannum CH, Wilcox CJ, Arend WP, Joslin FG, Dripps DJ, Himdal PL, Armes LG, Sommer A, Eisenberg SP, Thompson RC: Interleukin–1 receptor antagonist activity of a human interleukin–1 inhibitor. Nature 343:336–340, 1990.

Smith RJ, Chin JE, Sam LM, Justen JM: Biologic effects of an interleukin–1 receptor antagonist protein on interleukin–1 stimulated cartilage erosion and chondrocyte responsiveness. Arthritis Rheum 34:78–83, 1991.

Aren WP: Interleukin–1 receptor antagonist. Adv Immunol 54:167–227, 1993.

Arend WP, Welgus HG, Thompson RC, Eisenberg SP: Biological properties of recombinant human monocyte–derived interleukin 1 receptor antagonist. J Clin Invest 85:1694–1697, 1990.

Evans CH, Robbins PD: The interleukin–1 receptor antagonist and its delivery by gene transfer. Receptor 4:9–15, 1994.

Firestein GS, Berger AE, Tracey DE, Chosay JG. Chapman DL, Paine MM, Yu C, Zvaifler NJ: IL–1 receptor antagonist protein production and gene expression in rheumatoid arthritis and osteoarthritis synovium. J. Immunol 149:1054–1062, 1992.

Pelletier JP, et al.: Intraarticular injections with methylprednisolone acetate reduce osteoarthritic lesions in parallel with chondrocyte stromelysin synthesis in experimental osteoarthritis. Arthritis Rheum 37:414–423, 1994.

Pelletier JP, et al.: The in vivo effects of intraarticular corticosteroid injections on cartilage lesions, stromelysin, interleukin–1 and oncogene protein sysnthesis in experimental osteoarthritis. Lab Invest 72:578–586, 1995.

Rickard DJ, et al.: Proliferative responses to estradiol, IL–1 alpha and TGF beta by cells expressing alkaline phosphatase in human osteoblast–like cell cultures. Calcif Tissue Int 52:227–233, 1993.

Taichman RS, et al.: Effects of interleukin–1 beta and tumor necrosis factor–alpha on osteoblastic expression of osteocalcin and mineralized extracellular matrix in vitro. Inflammation 16:587–601, 1992.

Lethwaite et al. (1995) Annals of Rheumatic Diseases, vol. 54:pp. 591–596.

Cominelli et al. (1992) Gastro enterology, vol. 103, pp. 65–71.

Abraham et al. (1994) Lymphokine & Cytokine Res, vol. 13, No. 6, pp. 343–347.

Voelkel et al. (1994) Am. J. Respir. Cell. Mol. Biol. vol. 11, pp. 664–675.

METHOD OF TREATMENT OF OSTEOARTHRITIS WITH INTERLEUKEN-1 RECEPTOR ANTAGONIST

FIELD OF THE INVENTION

The invention relates to a method and a composition for the preventive treatment of osteoarthritis. More particularly the invention relates to a method and a composition for reducing the progression of lesion and cartilage degradation in osteoarthritis.

BACKGROUND OF THE INVENTION

Osteoarthritis, which is also called "degenerative joint disease", is the most common rheumatic disease and is characterized by a chronic inflammation of the articulation and a progressive depletion of articular cartilage matrix macromolecules. Together with the cartilage degeneracy, osteophytes (small abnormal body outgrowths) occur and develop on the stripped part of the articular bones. Symptoms of osteoarthritis occur in many people over the age of 65, and women are affected twice as often as men. These symptoms are pain, swelling and stiffness of the articulation. In a further stage of the disease, movement of articulations is limited and becomes painfil.

The most commonly used drugs for the treatment of osteoarthritis are the nonsteroidal anti-inflammatory agents (NSAID). Even though these drugs have proved effectiveness in relieving the symptoms of osteoarthritis and in decreasing osteoarthritis cartilage catabolism, some of them, like sodium salicylate, have shown inhibiting properties of the proteoglycan synthesis which may jeopardize the cartilage repair process. Other drugs, such as tiaprofenic acid, which do not inhibit the proteoglycan synthesis and have shown in vitro that they are able to decrease osteoarthritis cartilage catabolism, (Jean-Pierre Pelletier et al. *The Journal of Rheumatology* 1989;16:5, 646–655), have been unable to provide any preventing effect in development of osteoarthritis when administrated to patients suffering from the latter, (Edward C. Huskisson et al. *The Journal of Rheumatology* 1995; 22:10–1941–1946). Doxycycline, a member of the tetracycline family, was also shown to reduce, in vivo, the severity of osteoarthritis lesions in the dog ACL model while reducing metalloprotease activity, (Yu LP Jr et al. *Arthritis Rheum* 35:1150–1159, 1992). Recent data suggests that the action of corticosteroids is associated with a reduction in the synthesis of stromelysin-1 by chondrocytes. (see: Pelletier et al., *J Arthritis Rheum* 37:414–423, 1994; and Pelletier et al., *J Lab Invest* 72:578–586, 1995).

Accumulating evidence suggests that an important component of the matrix loss process is related to proteolytic enzyme activity which degrades the principal matrix macromolecules such as collagens and proteoglycans (aggrecans). Several matrix metalioproteases including stromelysin, collagenase, and gelatinase are believed to play an important role in matrix degradation. Support for the role of these enzymes in the arthritic process is found in observations showing that these proteases can be synthesized by chondrocytes and are present in increased amounts in pathological cartilage. Another important factor in osteoarthritis is the occurrence of synovial inflammation. There is compelling evidence that soluble inflammatory mediators such as cytokines, interleukin-1 (IL-1) and tumor necrosis factor-α a (TNF-(α), are involved in the osteoarthritis process. See for example:

Pelletier JP et al. *A textbook of Rheumatology*. Twelfih edition. Edited by DJ McCarthy, WJ Koopman. Philadelphia, Lea & Febiger, 1993;

Pelletier JP, et al. *J. In, Osteoarthritis*, Edition of Rheumatic Disease Clinics of North Ameria. Edited by R W. Moskowitz. Philadelphia, WB Saunders, 1993;

Pelletier JP et al. *J. Rheumatol* 22:109–114, 1995; and

Lanick JW et al. Kunkel SL. *Pharm Res* 5:129–139, 1988.

While cytokines and other mediators have been implicated in the core of the synthesis and release of matrix metalloproteases, IL-1 has also shown other deleterious effects on cartilage matrix metabolism. This cytokine, a product not only of mononuclear cells but also of synoviocytes and chondrocytes, has the ability to suppress the synthesis of collagen type II, characteristic of hyaline cartilage, while augmenting the synthesis of collagen type I collagen, characteristic of fibroblast cells (Goldring MB et al., *J Clin Invest* 30 82:2026–2037, 1988). In addition, IL-1 reduces aggrecan synthesis (Tyler JA. *Biochem J* 227:869–878, 1985. and Dingle JT et al., *Cell Biochem Funct* 9:99–102, 1991), the macromolecule largely responsible for the mechanical properties of articular cartilage.

Thus, this cytokine contributes both to reduce anabolic and enhance catabolic activities in affected joints.

A substance having inhibitory effects on the activity of IL-1 was found in conditioned monocyte medium: Arend WP et al., *J Immunol* 134:3868–3875, 1985, and in the urine of febrile patients : Balavoine JF et al., *J Clin Invest* 78:1120–1124, 1986. Characterizations of this molecule has revealed a 22 Kd protein and a specific competitive inhibitor of IL-1 known as IL-1 receptor antagonist or IL-Ira: Carter DB et al., *Nature* 344:633–638, 1990; and Hannum CH et al., *Nature* 343:336–340, 1990. This antagonist protein is a product of several cell types including monocytes, synoviocytes and chondrocytes and acts as a competitive inhibitor of IL-1 at the receptor level. In addition, IL 1ra binds with a greater affinity to the type 1 as compared to the type II IL-1 receptor. It has been shown that IL-1ra is capable of blocking some of the effects of IL-1, including the induction of matrix metalloproteins, nitric oxide, $PGE_2$ synthesis, as well as the expression of other cytokines (Smith RJ et al., *Adv Immunol* 54:167–227, 1993; Arend VP etal., *J Clin Invest* 85:1694–1697, 1990; and Evens CH et al. *Receptor* 4:9–15, 1994). Most of the above mentionned studies have demonstrated a relative deficit in the synthesis of IL-1ra vis-à-vis IL-1 in osteoarthritis and rheumatoid arthritis (RA) synovium.

To date, the majority of the studies exploring the effects of IL-1ra have been in vitro. Its in vivo effects have not been studied yet. Moreover some studies carried out in vivo have failed to demonstrate a therapeutic potential for rhIL-1ra in the treatment of arthritis. For instance, Arner, et al in *J Rheum* 22:1338–1346, 1995, reported that rhIL-1ra administrated intravenously fails to inhibit cartilage proteoglycan breakdown in polycation induced arthritis in the rabbit. Similarly it has been reported that intraperitoneal injections of rhIL-1ra does not affect the pathogenesis of antigen induced arthritis in mice (Wooley, et al, *Arthritis Rheum.* 36:1305–1314, 1993).

While the before mentioned drugs have met with limited success in the preventative treatment of osteoarthritis, new and improved method and pharmaceutical compositions are constantly being sought which may effectively reduce the progression of lesion and cartilage degradation in a mammal suffering from osteoarthritis. It is to such a method and a composition that the present invention is directed.

Surprisingly, the inventors have found that the periodic administration to a mammal of a composition comprising an amount of human recombinant Interleukin-1 receptor antagonist (rhIL-1ra) is effective for reducing the progression of lesions and cartilage degradation in a mammal suffering of osteoarthritis.

SUMMARY OF THE INVENTION

Therefor one of the objects of the invention is to provide a method for the preventative treatment of osteoarthritis comprising the periodic administration to a mammal of a composition comprising an amount of human recombinant Interleukin-1 receptor antagonist (rhIL-1ra) effective for reducing the progression of lesions and cartilage degradation. It is, of course, much preferred that the method be applied to patients suffering of this disease. Advantageously, the period of administration may range from a week to a month. It is also very much preferred that the administration of the composition be performed by intraarticular injection, even if subcutaneous injection or other known methods may also be contemplated. Preferably, Human recombinant Interleukin-1 receptor antagonist is injected intraarticularly in an amount ranging from 10 to 100 mg per injection.

Another object of the invention is to provide a composition for the preventative treatment of osteoarthritis comprising an amount of human recombinant Interleuldn-1receptor antagonist (rhIL-1ra) effective for reducing the progression of lesions and cartilage degradation and a pharmaceutically acceptable carrier. Advantageously, the carrier of such a composition is of a type suitable for the formulation of the composition for an intraarticular or subcutaneous injection, like a physiological saline solution. The amount of human recombinant Interleukin-1 receptor antagonist present in each dosage form may range from 10 to 100 mg per dosage.

Other objects, features and advantages of the present invention will be apparent from the following detailed description when read in conjunction with the accompanying figures and appended claims.

DETAILED DESCRIPTION OF THE INVENTION

Figure 1:
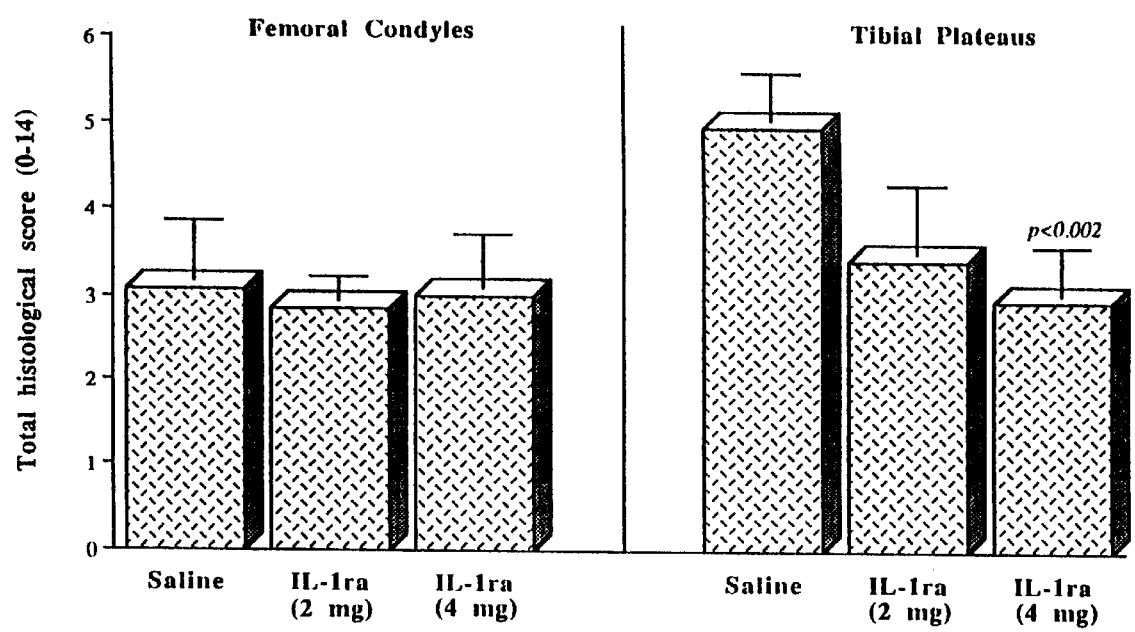
FIG. 1 represents histograms of the histological grading of lesion cartilage from femoral condyles and tibia plateaus of dogs four weeks after surgery, in accordance with the procedure of the example of the invention.

As indicated hereinabove, the present invention is directed to both a method and a composition for the treatment of osteoarthritis in a mammal and more especially in a human being, by the use of a therapeutic dosage of rhIL-ra. The invention is based on the discovery that intraarticular injections of rhIL-1ra reduces the osteophyte formation and severity of cartilage lesions in osteoarthritis in a dose-dependent fashion.

At the opposite of several drugs already known in the art for having preventing effect for treating osteoarthritis only in vitro, use of rhIl-1ra has shown effectiveness in-vivo to reduce the progression of lesions and cartilage degradation in mammal suffering of osteoarthritis.

Although the specific mechanism(s) responsible for this effect remains unknown, it is believed that growth factors and cytokines are involved in the development of osteophytes in osteoarthritis. It is possible that the reduction in incidence and size of osteophytes in this model result from the inhibition of direct or indirect effects of IL-1 on osteoid deposition in treated animals (Rickard DJ et al., *Calcif Tissue Int.* 52:227–233, 1993.; and Taichman RS et al., *Inflammation* 16:587–601, 1992). Along with mechanical factors, growth factors and cytokines may be involved in the formation and growth of osteophytes, since these molecules can induce growth and differentiation of mesenchymal cells (Van Beuningen HM et al., *Lab Invest* 71:279–290, 1994.; Arend WP. *In, Primer on the Rheumatic Diseases*. Tenth edition. Edited by HR Schumacher, JH Klippel, WJ Koopman. The Arthritis Foundation, Georgia, 1993). Injections of TGF-β in the murine knee joint induces the outgrowth of chondroid tissue at the femoral ridges. Additionally, inhibition of IL-1 effect would decrease cell mitosis rate and hence modulate the action of TGF-β by reducing the biological effect of this growth factor (Vivien D et al., *J Cell Physol* 143:534–545, 1990). Thus, it is conceivable that the increase in the local synthesis of growth factors or proinflammatory cytokines by the inflamed synovium may be an important factor in osteophyte formation.

The present invention will be illustrated in detail in the following example. This example is include for illustrative purposes and should not be considered to limit the present invention.

EXAMPLE

A canine ACL model of osteoarthritis has been used in the present example to examine the action of intraarticular injections of rhIL-1ra on the development of osteoarthritic lesions as well as the expression of metalloproteases, collagenase-1 and stromelysin-1. Osteoarthritis has been artificially induced in dogs by transection of the anterior cruciate ligament (ACL) of the dog's knee which leads to articular changes resembling the morphological and biochemical changes observed in human osteoarthritis (Brandt KD et al. *Arthritis Rheum* 34:1560–1570, 1991). Similar to naturally-occurring disease in man metalloproteases known as collagenase-1, stromelysin-1 and cytokines such as IL-1 are significantly increased in the osteoarthritis cartilage and synovial membrane of the experimental dog model (Yu LP Jr et al., *Arthritis Rheum* 35:1150–1159, 1992). This model has proven to be useful for testing the effects of drugs on disease progression and the study of the main pathophysiological mechanisms involved in cartilage degradation (Pelletier JP et al., *Arthritis Rheum* 37:414–423, 1994). For example, corticosteroids have demonstrated, both under therapeutic and prophylactic conditions, a reduction in the progression of cartilage erosion and osteophyte formation (Pelletier JP et al., *J Arthritis Rheum* 37:414–423, 1994). Therefore, the canine ACL model of osteoarthritis has been used in the present example to be extended to mammal and more particularly to human being, as this model is one of the more suitable for human.

METHODS

Experimental Groups

A total of 16 cross-bred dogs, each weighing 20 to 25 kg each were used in the study. The ACL of the right knee of each dog was transected via a stab incision under general anaesthesia: Pelletier JP et al., *J Arthritis Rheum* 37:414–423, 1994. Dogs were randomly assigned to 3 groups. The first group (n=5) received intraarticular injections of sterile physiological saline solution (1 ml) twice weekly beginning at the time of surgery. The second group (n=6) received injections of rhIL-1ra (2 mg) (Amgen/Synergen, Boulder, Colo.) in 1 ml of sterile physiological saline solution using the same schedule as the first group.

The third group of dogs (n=5) received intraarticular injections of rhIL-1ra (4 mg) in 1 ml of physiological saline solution at the same frequency as the first two groups. All dogs were sacrificed 4 weeks post-surgery. The saline control group was included in the protocol in order to evaluate the effect of the IL-1ra vehicle solely on the disease progression. The dogs were kept in animal care facilities within for 1 week after surgery and then sent to a housing farm where they were left free to exercise in a large field for 4 to 6 hours every day.

Dissection and Macroscopic Grading

Immediately after the sacrifice, the right knees of the dogs were removed, the synovial fluid aspirated and dissection was performed aseptically on ice. Each knee was examined blindly by two independent observers for gross morphologic changes, including the presence of osteophyte formation and cartilage lesions: Pelletier JP et al., *J Arthritis Rheun* 37:414–423, 1994. The degree of osteophyte formation was graded by measuring the maxmal width (mm) of the spur on each femoral condyle. The cartilage changes of the medial and lateral femoral condyles and tibial plateaus were each graded separately under a dissecting microscope (Stereozoom®, Bausch & Lomb, Rochester, N.Y.). The depth of the erosion was graded on a scale of 0 to 4, with 0 representing a normal surface appearance, and 4 a cartilage erosion extending to the subchondral bone. The surface area (size) of articular surface lesions was measured and expressed in $mm^2$. These results are shown on table I.

TABLE I

MACROSCOPIC LESIONS ON FEMORAL CONDYLES AND TIBIAL PLATEAUS IN OA DOGS.

| Osteo-arthritic Group* | No of animals | Femoral condyles Size, ($mm^2$) | Grade, (0–4 scale) | Tibial plateaus Size, ($mm^2$) (p)② | Grade, (0–4 scale) (p)② |
|---|---|---|---|---|---|
| Saline | 5 | 4.70 ± 2.80 | 1.20 ± 0.29 | 24.40 ± 8.17 | 1.20 ± 0.29 |
| rhIL-ra (2 mg) | 6 | 3.42 ± 0.97 | 0.75 ± 0.22 | 20.90 ± 8.01 | 1.00 ± 0.26 |
| rhIL-ra (4 mg) | 5 | 1.40 ± 0.71 | 0.40 ± 0.22 | 7.70 ± 5.16 ($p < 0.04$) | 0.30 ± 0.21 ($p < 0.04$) |

*After surgery, the dogs were treated twice a week with intraarticular injections of either saline, 2 mg or 4mg rhIL-1ra, for 4 weeks and sacrified.
②Statistical analysis was done by Mann Whitney U-test; p values as compared to OA-saline group.

Histopathology

Histologic evaluation was performed on full thickness sagittal sections of cartilage from the entire lesional surfaces of each femoral condyle and tibial plateau: Pelletier et al., *J Arthritis Rheum* 37:414–423, 1994. Each specimen was dissected and fixed in 10% buffered formalin and embedded in paraffin for histologic study. Serial sections (5 μm) were prepared and stained with safranin-0. The severity of the osteoarthritis lesions was graded on a scale of 0 to 14 by two independent observers using the histologic-histochemical scale ofMankin, et al., *J Bone Joint Surg Am* 53:523–537, 1971., and the results are shown in FIG. 1. The remaining cartilage specimens were rinsed with cold saline and immediately frozen at −80° C.

Representative specimens of the synovial membrane from the medial and lateral compartments of the knee were dissected from the underlying tissues, Pelletier et al., *Jr. Arthritis Rheum* 28:554–561, 1985. Briefly, the specimens were fixed in 10% buffered formalin, embedded in paraffin, sectioned (5 μm) and then stained with hematoxylin-eosin. For each compartment, two synovial membrane specimens were examined for scoring purposes. The highest score from each compartment was averaged and considered as a unit for the whole knee. The severity of synovitis was graded on a scale of 0 to 10 by two independent observers (Goldring MB, Birkhead J, Sandell LJ, Kimura T; Krane SM. *J Clin.Invest* 82:2026–2037, 1988), by adding the scores of three histologic criteria: (i) synovial lining cell hyperplasia (0 to 2+); (ii) villous hyperplasia (0 to 3+); (iii) the degree of cellular infiltration by mononuclear and polymorphonuclear cells (0 to 5). The remaining synovial membrane was rinsed in cold saline and immediately frozen at −90° C.

IL-1ra ELISA Assay

The concentration of rhIL-1ra in the synovial fluid of dogs treated with intraarticular injections of rhIL-1ra was determined by using a commercial immunoassay kit (Quantikine® Human IL-1ra; R & D Systems, Minneapolis, Minn.). Two hundred microliters of each synovial fluid sample were tested following the manufacturer's instructions. The limit of detection of the assay is 6.5 pg/ml.

RNA Extraction

Total RNA was isolated from cartilage. Cartilage samples were homogenized in 10 volumes of 6M guanidine hydrochloride containing 25 mM sodium citrate, pH 7,25 mM EDTA, 0.5% sarkosyl and 100 mM 2-mercaptoethanol, followed by addition of 0.1 volume of 3 M sodium acetate buffer, pH 5, 0.25 volume of saturated phenol, and 0.25 volume of isoamyl alcohol/chloroform (1:49). The solution was vigorously shaken and cooled at 4° C. for 1 hour. The mixture was centrifuged (12,000 g, 30 minutes, 4° C.), the aqueous phase removed, mixed with 1 volume of isopropanol and allowed to stand at −20° C. for 18 hours. After a second centrifugation (12,000 g, 20 minutes, 4° C.), the pellet was resuspended in 10 ml of 4M guanidine isothiocyanate (GIT) buffer containing 3.3 ml of cesium trifluoroacetate (2.01 gm/ml; Pharmacia Biotech, Baie d'Urfé, Québec) and centrifuged for 24 hours (13eckman® SW 40 Ti rotor, 100,000 g, 4° C.). The resultant pellet was dissolved in 20 mM sodium acetate buffer, pH 5, 0.5% sodium dodecyl sulfate (SDS), 1 mM EDTA and extracted once with pre-heated (60° C.) saturated phenol. The RNA was precipitated with 3 volumes of absolute ethanol and maintained at −20° C. for 18 hours. After being centrifuged (13,000 g, 20 minutes, 4° C.), the RNA pellet was solubilized in DEPC-treated water, and the RNA quantitated spectrophotometrically.

Total RNA was extracted from the synovial membrane as described for cartilage, with the following modifications; the initial buffer used was 4 M GTT, after isopropanol precipitation the pellet was directly extracted using a 20 mM sodium acetate buffer.

Northern Blotting

Total RNA were resolved on 1.2% agarose-formaldehyde gels and 3 μg of RNA were used for specimens from cartilage and 10 μg for those from the synovium. Following transfer to nylon membranes (Hybond® N, Amersham Corp., Oakville, Ontario) overnight at 4° C. in 10 mM sodium acetate buffer, pH 7.8, containing 20 mM Tris and 0.5 mM EDTA, the RNA was cross-linked to the membranes by exposure to ultraviolet light.

Specific sets of primers for collagenase-1, stromelysin-1 and GAPDH were developed. A 460 bp, a 274 bp, and a 272 bp primer were constructed, respectively, from the ligation of a DNA polymerase chain reaction fragment amplified from canine synovial fibroblasts (collagenase-1, stromelysin-1) or chondrocyte (GAPDH) RNA to Bluescript vector. The primers were subsequently sequenced, in order to verify the identity of the genes.

The oligonucleotide primers were prepared with a DNA synthesizer (Cyclone Model (trade name), Miffipore, Bedford, Mass.) and used at a final concentration of 200 nM. The sequences for collagenase-1 primers were 5'-CCAAAAGCGTGTGACAGTAAGC-3' (sense primer) which corresponded to position 891–912 bp of the sequence of the human gene publkished in Goldberg el al., *J Biol. Chem* 261:6600–6605, 1986. and 5'-CAACTTTGTGGCCAATTCCAGG-3' (antisense primer) from position 1326–1347 bp. The sequences for stromelysin-1 primers were 5'-GAAAGTCTGGGAAGAGGTGACTCCAC-3' (sense primer) and 5'-CAGTGTTGGCTGAGTGAAAGAGACCC-3' (antisense primer), corresponding to positions 414–440 bp and 671–697 bp, respectively, of the sequence published in Saus et al., *J Biol Chem* 263:6742–6745, 1988. The sequences for GAPDH primers were 5'-CAGAACATCATCCCTGCCTCT-3' (sense primer), which corresponded to position 604–624 of the published sequence of the human gene, (Tso et al., Nucleic Acids Res. 13:2485–2502, 1985) and 5'-GCTTGACAAAGTGGTCGTTGA-3' (antisense primer), which corresponded to position 901–922 bp.

Detection was done with a luminescent method using Digoxigenin-11-Uridyl Triphosphate (DIF-11dUTP) (Boehringer Mannheim Biochemica, Mannheim, Germany) with Lumigen PPD [4-Methoxy4-(3-phosphatephenyl) Spiro-(1,2-dioxetane-3,2'-adamant ane) disodium salt] as substrate for alkaline phosphatase conjugated to anti-DIG antibody Fab-fragments, The membranes were then subjected to autoradiography using Kodak XAR5® films (Eastman Kodak LTD, Rochester, N.Y.) at room temperature. Each membrane was probed, first for coliagenase-1 or stromelysin- 1, then stripped and reprobed with GAPDH. The stripping buffer consisted of 50 mM Tris-HCl, pH 8, containing 60% formamide and 1% SDS. The membrane was heated at 75° C. for 1 hour, rinsed thoroughly in distilled water and probed again starting at the prehybridization step. After exposure, all autoradiograph films were subjected to laser scanning densitometry (GS-300 (trade name), Hoefer Scientific Instruments, San Francisco, Calif.) to determine relative mRNA abundance. Standardization against GAPDH MRNA levels enabled the quantitative evaluation of specific mRNA. Relative expression of coflagenase-1 and stromelysin-1 were calculated as the ratio of the relative intensity of the metalloprotease band to the relative intensity of the GAPDH band.

Statistical Analysis

The data were expressed as mean± SEM and when appropriate analyzed with the Mann-Whitney U-test. A p value equal to or less than 0.05 was considered significant.

RESULTS

IL-1ra Synovial Fluid Levels

Human rhIL-1ra was detectable by ELISA assay in the synovial fluid collected at time of sacrifice from all dogs treated with the antagonist. The level in the dogs treated with 2 mg injections was lower (103.8±86.9 ng/ml) than those treated with the 4 mg injections (153.3±132.1 ng/ml).

Macroscopic Grading

Osteophytes

Osteophytes were present on 70% of condyles in the saline-treated dogs. The mean width of osteophytes in these dogs was 2.3±0.7 mm. In general, when present, the osteophytes were observed on both condyles and their sizes were similar. Dogs treated with rhIL-1ra presented a dose-dependent decrease in the incidence and size of osteophytes on condyles. Dogs treated with the 2 mg rhIL-1ra injections has a lower incidence (42%) and smaller osteophyte size (0.7±0.3 mm) than the control group. The reduction in dogs treated with 4 mg rhIL-1ra injections was even more pronounced than the previous group, with a reduction in the incidence of osteophytes to 20% ($p \leq 0.06$) and mean size to 0.5±0.3 mm ($p \leq 0.04$).

Cartilage Lesions

In saline-treated dogs, fibrillated lesions usually of a small size and low grade were present on both condyles (Table I). Both groups of dogs treated with rhIL-1ra presented a reduction in the size and/or the grade of condyle lesions. However, the effect was more pronounced in the dogs treated with the 4 mg injections (Table I). The tibial plateau lesions in the saline-treated dogs were similar on both plateaus and were more severe than on the femoral condyles, particularly with regards to their size, which was much larger (Table I). Dogs treated with rhIL-1ra injections at a dosage of2 mg had lesions that were slightly less severe compared to the saline-treated dogs. As for femoral condyles, the dogs treated with 4 mg rhIL-1ra injections presented a marked and statistically significant reduction ($p \leq 0.04$) in both size and grade (Table I).

Synovial Membrane

Synovium from saline-treated dogs showed definite signs of synovial inflammation with a yellowish-red discoloration and a large number of blood vessels. Both goups of dogs treated with rhIL-1ra demonstrated similar changes as the control group, except that they generally had a more pronounced tissue discoloration and thickening.

Microscopic Grading

Cartilage

Specimens from the saline-treated dogs showed morphological changes characteristic of osteoarthritis. These included fibrillation and fissures of the cartilage surface, loss of safranin-0 staining, as well as an increase in tissue cellularity and cloning. There was no tidemark invasion by blood vessels in the samples studied.

Figure 2:
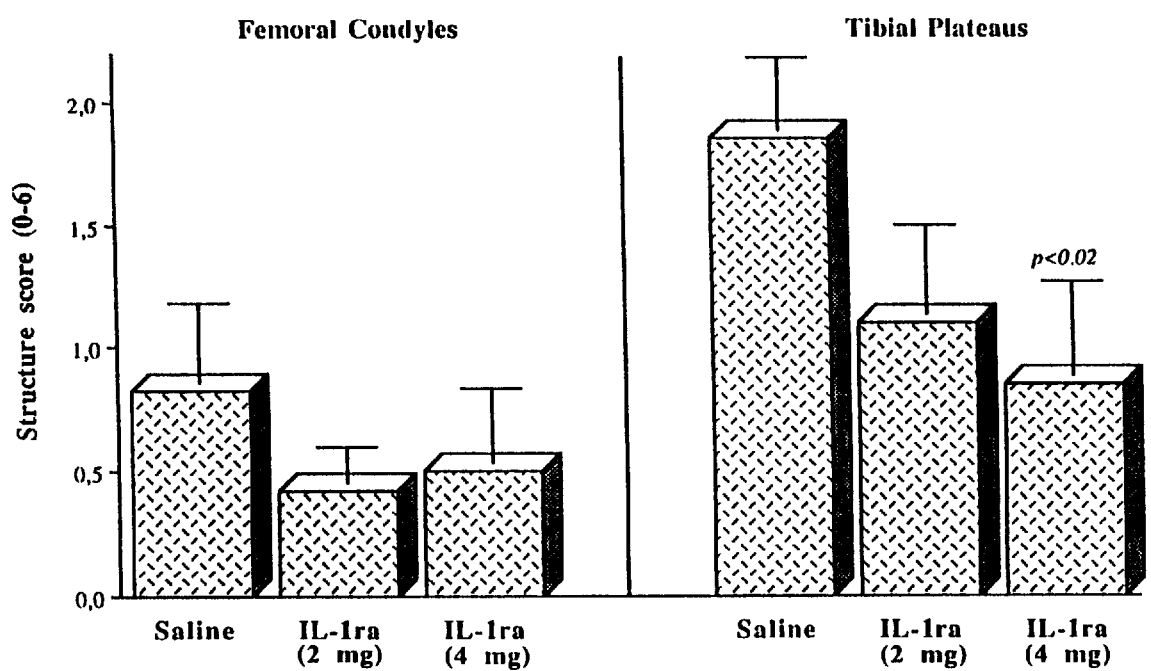
FIG. 2 represents histograms of structural changes grading of cartilage from femoral condyles and tibia plateaus of dogs four weeks after surgery, in accordance with the procedure of the example of the invention.

The total score of histological lesions on femoral condyles (3.06±0.69) was less severe than those on tibial plateaus (FIG. 1). Although no significant effect on the total score of femoral condyle lesions was observed in both rhIL-1ra treated groups when compared to controls, a trend towards less severe structural changes was observed (FIG. 2). The score for structural changes (0–6 scale; FIG. 2) was 0.8±0.3 in the saline-treated dogs, 0.4±0.1 and 0.5±0.3 for the 2 mg and4 mg rIL-1ra-treated groups, respectively.

Interestingly, the total histological score (FIG. 1) of lesions on tibial plateaus was less severe in the dogs treated with rhIL-1ra compared to the control group (FIG. 1). The dogs treated with 2 mg rhIL-1ra injections had a total lesion score of 3.40±0.79 ($p \leq 0.002$; FIG. 1) for the 4 mg rhIL-1ra treated dogs. The reduction in the severity of lesions was particularly noticeable for structural changes (0–6 scale; FIG. 2) and tissue cellularity (0–3 scale). With regards to the structure, values of 1.1±0.4 and 0.9±0.4 ($p \leq 0.02$) were obtained for the 2 mg and 4 mg treated groups, and 1.9±0.3 for the control group, whereas 0.9±0.3, 0.9±0.2 ($p \leq 0.005$) and 1.6±0.1 were obtained for the 2 mg, 4 mg rhIL-1ra treated groups and control group, respectively, for the cellularity.

Synovial Membrane

A moderate inflammatory reaction was present in specimens from the three groups with similar total histological scores. The scores were 5.10±0.71, 4.58±0.45, an 5.20±0.34 for the saline, 2 mg and 4 mg rhIL-1ra-treated groups, respectively. However, qualitative differences in synoial inflammation were observed between rhIL-1ra-treated and control dogs. Specimens from rhIL-1ra-treated dogs had higher scores for mononuclear cell infiltration (0–5 scale) (2 mg, $2.83\pm0.31$, $p\leq0.05$; 4 mg, $2.50\pm0.27$) compared to thesaline-treated dogs ($1.80\pm0.44$).

Metalloprotease Expression

The level of expression of collagenase-1 and stomelysin-1 in the synovial membrane and cartilage were measured. In the synovium, the levels of expression for collagenase-1 and stromelysin-1 were similar among the three groups. However, the levels of collagenase-1 and stromelysin-1 MRNA in cartilage showed differences. The stromelysin-1 expression demonstrated a slight decrease only for the 2 g rhIL-1ra-treated-groups when compared to the saline-treated group. In contrast, the collagenase-1 mRNA level was significanly lower ($p\leq0.005$) in both rhIL-1ra-treated groups.

DISCUSSION

The above example demonstrates that intraarticular injections of rhIL-1ra reduced the osteophyte formation and severity of cartilage lesions in the canine ACL model of OA in a dose-dependent fashion. The fact that the effect is more pronounced in the group receiving the higher dose of rhIL-1ra, is an additional argument for suggesting the role of IL-1 in the genesis of osteophytes.

The injections of rhIL-1ra induced a reduction in both the macroscopic and the microscopic lesion scores in condyles and plateaus, the reduction being more pronounced on plateaus, however. The reduction of macroscopic lesions was noted for the size as well as the depth of the cartilage lesions. A preferential effect of drugs on tibial plateau lesions has already been reported and may be explained by the fact that on the plateaus, lesions are more severe than on the condyles. The chondroprotective effect of rhIL-1ra was dose-dependent and more pronounced at 4 mg than at 2 mg. On the plateaus, the reduction in histological grades of lesions was essentially the result of a better conservation of the cartilage structure, and a reduction in cell cloning. In condyles, although the total histological score was not improved, one could note a decrease in the severity of structural changes. These findings emphasized the possibility that the inhibition of IL-1 activity was responsible, at least in part, for these improvements. IL-1 has been shown to have some mitogenic effects on articular chondrocytes, in vitro, Frazer et al., *Biochim Biophys Acta* 1226:193–200, 1994 and it is capable of modulating the mitogenic activity of certain growth factors, including TGF-β, (Guerne et al. *J Cell Physiol* 158:476–484, 1994 and Pujol et al. *Endocrinol* (Paris) 55:109–120, 1994). Alternatively, it is possible that the reduced incidence of chondrocytic hypercellularity observed in treated dogs was indirectly related to the inhibition of IL-1 activity, although it was a secondary effect, since the inhibition of synthesis of oncoproteins like c-Myc, c-Fos and c-Jun have mitogenic effects. This hypothesis is supported by recent studies showing that in the dog ACL model intraarticular corticosteroid injections reduced the severity of osteoarthritis lesions and chondrocyte cloning while simultaneously suppressing oncoprotein synthesis (Pelletier et al. *J Lab Invest* 72:578–586, 1995).

Northern blotting analysis indicates that there was an important collagenase-1 expression suppressive effect of rhIL-1ra in cartilage. This in vivo reduction by a known specific inhibitor of IL-1 again strongly supports the contention that this cytokine is an important mediator of this metalloprotease synthesis. Surprisingly, no dramatic difference was observed in the cartilage expression of stromelysin-1 in the rhIL-1ra-treated dogs, nor were important differences noted in the expression levels of these two metalloproteases in the synovial membrane. Either IL-1 is not a pivotal mediator of stromelysin-1 synthesis in this model, at least during the early stage, or that uncharacterized intraarticular conditions maintained stromelysin-1 expression despite the inhibition of IL-1 activity. Alternatively, perhaps even a very low level of IL-1 receptor occupancy by IL-1 suffices to induce the expression of stromelysin-1. However, the observation of differences in expression between collagenase-1 and stromelysin-1 is not totally surprising as discoordinate expression of these two metalloprotease genes has been previously reported (Nguyen et al., *J Biol Chem* 265:17238–17245, 1990). Moreover, it is possible that the reduction in collagenase-1 expression was responsible for the preservation of the collagenous architecture of the cartilage. This hypothesis is supported by the histological findings, in which the cartilage from the rhIL-1ra-treated dogs demonstrated a much lower incidence in structural damage. The histological score from the two rhIL-1ra-treated groups was approximately half that of the saline-treated dogs, both for the femoral condyles and the tibial plateaus. This finding suggests that rhIL-1ra was capable of reducing matrix damage, principally collagen type II, possibly by inhibiting IL-1-mediated collagenase synthesis. On the other hand, the absence of improvement in the the safranin-O staining in rhIL-1ra-treated dogs, suggesting that the depletion in cartilage proteoglycan was minimally affected, is not surprising in view of the continued expression of stromelysin-1.

The weaker effect from the higher dosage of rhIL-1ra at suppressing collagenase-1 expression is intriguing and contrasts with its greater chondroprotective effect. Should one believe that the chondroprotective action of rhIL-1ra be directly related to its suppressive effect on metalloprotease synthesis, then a dose-dependent suppression would be expected.

While the invention has been described with respect to certain specific embodiments, it will be appreciate that many modifications and changes may be made by those skilled in the art without departing from the spirit of the invention. It is intended, therefore by the appended claims to cover all such modification and changes as fall within the true spirit and scope of the invention.

We claim:

1. A method for treating osteoarthritis comprising the periodic administration by intraarticular injection to a mammal suffering from this disease, of a composition comprising an amount of Human recombinant Interleukin-1 receptor antagonist effective for reducing the progression of lesions and cartilage degradation, said administration being made over a period ranging from a week to a month.

2. A method for treating osteoarthritis comprising the periodic administration by intraarticular injection to a patient suffering from this disease, of a composition comprising an amount of Human recombinant Interleukin-1 receptor antagonist effective for reducing the progression of lesions and cartilage degradation, said administration being made over a period ranging from a week to a month.

3. The method of claim 2, wherein Human recombinant Interleukin-1 receptor antagonist is administered in an amount ranging from 10 to 100 mg per injection.

* * * * *